(12) United States Patent
Basham et al.

(10) Patent No.: US 8,585,870 B2
(45) Date of Patent: Nov. 19, 2013

(54) PROCESS TO C-MANUFACTURE ACRYLONITRILE AND HYDROGEN CYANIDE

(75) Inventors: Brent E. Basham, Cordova, TN (US); Richard Thomas Stimek, Mt. Juliet, TN (US)

(73) Assignee: E I du Pont de Nemours and Company, Wilmington, DE (US)

( * ) Notice: Subject to any disclaimer, the term of this patent is extended or adjusted under 35 U.S.C. 154(b) by 1222 days.

(21) Appl. No.: 12/074,775

(22) Filed: Mar. 5, 2008

(65) Prior Publication Data

US 2009/0223804 A1  Sep. 10, 2009

(51) Int. Cl.
*B01D 3/34* (2006.01)

(52) U.S. Cl.
USPC .............. 203/29; 203/38; 203/42; 203/61; 203/96; 203/DIG. 3; 422/610

(58) Field of Classification Search
USPC .............. 203/8, 29, 38, 42, 61, 85, 96, 35, 203/DIG. 3; 558/463, 466
See application file for complete search history.

(56) References Cited

U.S. PATENT DOCUMENTS

| | | | | |
|---|---|---|---|---|
| 3,185,636 A * | 5/1965 | Stevens et al. | ................. | 203/8 |
| 3,911,089 A | 10/1975 | Shiraishi et al. | | |
| 4,234,510 A | 11/1980 | Wu | | |
| 4,238,295 A * | 12/1980 | Odom | ............... | 203/83 |
| 4,377,444 A * | 3/1983 | Wu | ................. | 203/96 |
| 4,434,029 A * | 2/1984 | Kurihara et al. | ............... | 203/42 |
| 4,485,079 A | 11/1984 | Brazdil, Jr. et al. | | |
| 4,965,060 A | 10/1990 | Tsukahara et al. | | |
| 5,204,079 A * | 4/1993 | Suresh et al. | ............... | 423/376 |
| 5,288,473 A | 2/1994 | Shaw et al. | | |
| 5,629,444 A * | 5/1997 | Gibson et al. | ............... | 558/466 |
| 5,840,648 A | 11/1998 | Suresh et al. | | |
| 5,869,730 A * | 2/1999 | Graham et al. | ............... | 558/320 |
| 5,882,618 A | 3/1999 | Bhatia et al. | | |
| 6,084,121 A | 7/2000 | Rogers et al. | | |
| 6,204,407 B1 | 3/2001 | Godbole et al. | | |
| 6,238,574 B1 * | 5/2001 | Cesa et al. | ............... | 210/763 |

(Continued)

FOREIGN PATENT DOCUMENTS

| CN | 1031662 | 3/1989 |
|---|---|---|
| DE | 1238011 | 4/1967 |

(Continued)

OTHER PUBLICATIONS

Weissermel, K. , Arpe, H."Industrial Organic Chemistry", 4th edition, Wiley-VCH Verlag GmbH & Co KGaA, Weinheim. ISBN 3-527-30578-5, 2003, p. 43.*

(Continued)

*Primary Examiner* — Robert A Hopkins

(57) ABSTRACT

A process for co-manufacture of acrylonitrile and hydrogen cyanide comprises combining a stream comprising hydrogen cyanide and an acrylonitrile reactor product stream, to produce a combined product stream, having a ratio of acrylonitrile to hydrogen cyanide of about 9 to 1 or less, which can be varied; and treating the combined product stream in a recovery/purification system of acrylonitrile process wherein pH is controlled by addition of an acid to prevent HCN polymerization. The ratio of acrylonitrile to hydrogen cyanide is generally between 2 to 1 and 9 to 1. The stream comprising hydrogen cyanide is advantageously a hydrogen cyanide product stream from a hydrogen cyanide synthesis reactor.

18 Claims, 1 Drawing Sheet

(56) References Cited

U.S. PATENT DOCUMENTS

| | | |
|---|---|---|
| 6,287,531 B1 | 9/2001 | Riegert et al. |
| 6,296,739 B1 | 10/2001 | Godbole |
| 6,315,972 B1 | 11/2001 | Mehdizadeh et al. |
| 6,355,828 B1 | 3/2002 | Rogers et al. |
| 6,413,485 B2 | 7/2002 | Seely et al. |
| 6,596,251 B2 | 7/2003 | Schaefer et al. |
| 6,743,407 B2 | 6/2004 | Schaefer et al. |
| 6,793,776 B2 * | 9/2004 | Godbole .................... 203/6 |
| 7,070,743 B2 | 7/2006 | Blackwell et al. |
| 2004/0267054 A1 * | 12/2004 | Ward et al. ................ 568/594 |
| 2005/0047988 A1 | 3/2005 | Kim |
| 2006/0235088 A1 | 10/2006 | Olah et al. |
| 2007/0056841 A1 * | 3/2007 | Agarwal et al. ............ 204/164 |

FOREIGN PATENT DOCUMENTS

| | | |
|---|---|---|
| JP | 51016615 | 2/1976 |
| JP | 2003002870 A | 1/2003 |
| WO | WO 03/018541 A1 | 3/2003 |

OTHER PUBLICATIONS

Langvardt, P.W., "Acrylonitrile", Ulmann's Encyclopredia of Industrial Chemistry, Wiley-VCH Verlag GmbH & Co (c) 2005.*

Kirk-Othrner—Acrylonitrile Article, pp. 1-17.

Mafezzoni, Hydrocyanic acid and acrylonitrile from methane; Riv. Combustibili (1954), 8, 795-803; Inst. richerche Guido Donegani, Novara, Italy. Abstract Anon., Natural gas to acrylonitrile. American Cyanamid's new Fortier plant uses direct acetylene-HCN process; Oil and Gas Journal (1955), 54(18), 110-113. Abstract.

Bobkov, Production of hydrocyanic acid and acrylonitrile; Khimicheskaya Nauka i Promyshlennost (1957), 2, 34-45. Abstract.

Smith, A study in the recovery of unaccountable hydrogen cyanide losses in an acrylonitrile industrial process; Diss. Abstr. Int., B 2000, 61(4), 2078; Texas A and M Univ., College Station, Texas, USA. Abstract.

* cited by examiner

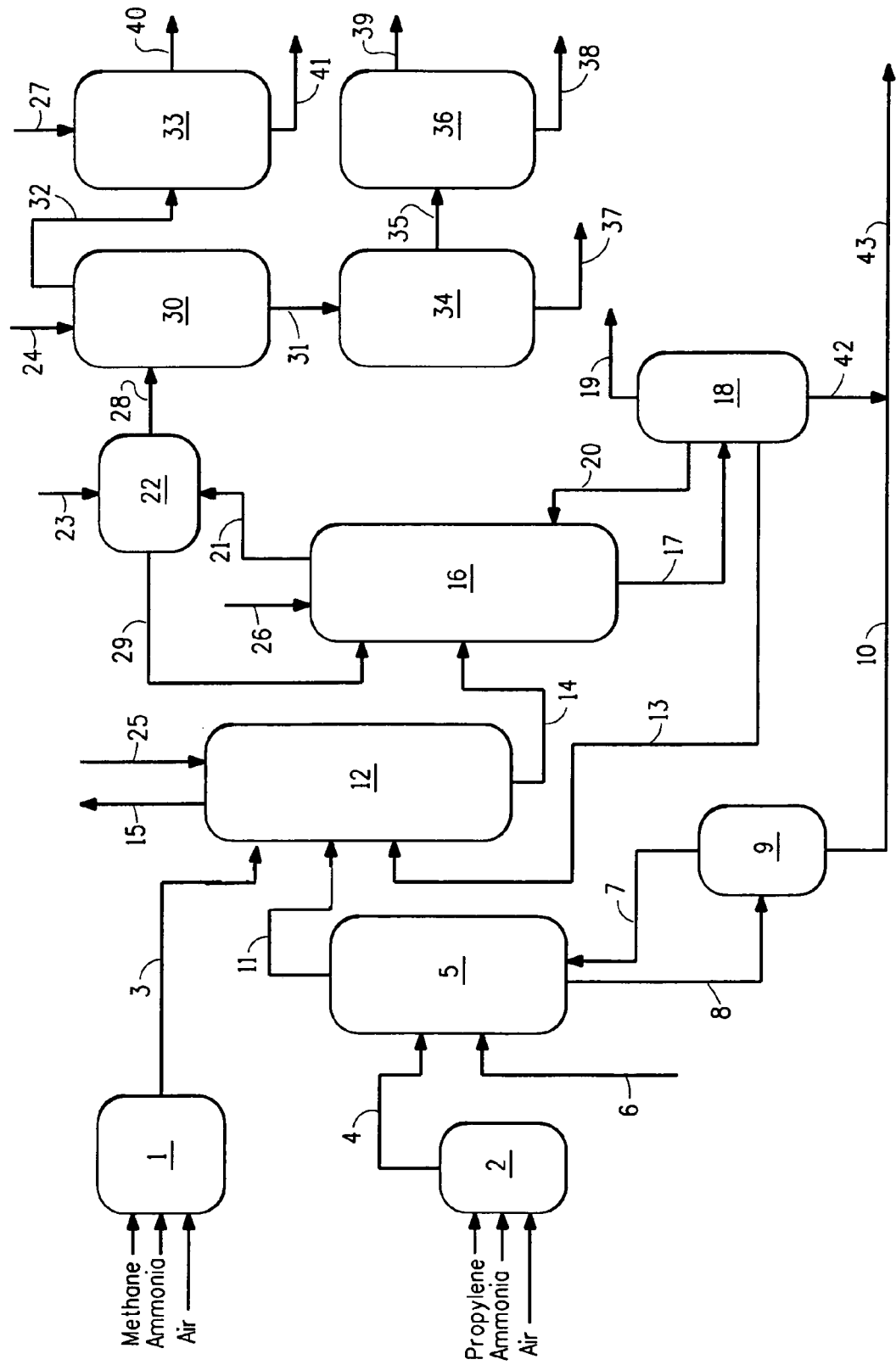

PROCESS TO C-MANUFACTURE ACRYLONITRILE AND HYDROGEN CYANIDE

FIELD OF THE INVENTION

This invention relates to a process for the co-manufacture of acrylonitrile and hydrogen cyanide with improved control and efficiency.

BACKGROUND OF THE INVENTION

Acrylonitrile (ACRN) is an important monomer for the synthesis of various polymers including acrylic fibers, synthetic rubbers, nylons, and is the starting material for acrylic acids and acrylaminde. Processes to prepare acrylonitrile are well known, and include the so-called "Sohio Process" in which propylene/propane react with ammonia and oxygen (air) over a catalyst at elevated temperatures ("ammoxidation"). Hydrogen cyanide (HCN) and acetonitrile ($CH_3CN$) are produced as by-products.

HCN is a valuable by-product due to it vast uses as a starting material or as an intermediate. HCN is used, for example, as a starting material for the synthesis of various polymers, including polyamides, and chemicals. HCN is the starting material for metal cyanides including sodium cyanide and potassium cyanide, two compounds important in metallurgy for recovery of gold and the hardening of steel.

To increase HCN yield in the Sohio process, a technique commonly referred to as "methanol injection" may be employed. Methanol injection involves adding methanol gas to the acrylonitrile reactor or feed to the reactor to increase HCN production. A conventional Sohio process produces a weight ratio of acrylonitrile to HCN of about 9 to 1, whereas using methanol injection, this ratio can be decreased to 8 to 1. In a typical plant, use of methanol injection can result in an increase of about 10 million pounds of HCN per year with coproduction of about 360 to 400 million pounds of acrylonitrile per year.

Methanol injection has several disadvantages. Due to the burden placed on the system, overall yield of acrylonitrile can be reduced by as much as 5%. Methanol reduces propylene content of the reactor, resulting in less acrylonitrile being produced. High heat released at the catalyst surface as methanol reacts leads to catalyst deactivation resulting in more frequent catalyst replacement. Methanol can also react with ammoxidation intermediates to form reactive intermediates that can lead to polymer formation and fouling in downstream equipment.

Methanol also reacts with oxygen in the system, consuming this reagent, and forming undesired by-products, such as carbon oxides.

Less obvious disadvantages of methanol injection process are increased cost for equipment and energy due to the need to convert methane to methanol. Methanol is typically produced by reaction of methane with steam under high temperatures and pressures over a copper catalyst yielding carbon monoxide and hydrogen, commonly referred to as "synthesis gas" or "syn-gas." The syn-gas then undergoes an additional high temperature reaction to yield methanol. It is desirable to avoid the inefficiencies of an intermediate step to convert methane to methanol while increasing production of HCN in an ACRN reaction system.

Other alcohols and ketones have been added to increase production of HCN in an acrylonitrile process. While such processes increase the HCN to ACRN ratio, the total pounds of acrylonitrile is reduced, and adding additional alcohols and ketones to the reactor, further accelerates catalyst deactivation.

HCN is a highly toxic and flammable gas. At high concentrations, risk increases for exothermic runaway reaction through polymerization and decomposition, which is a potentially explosive situation. Therefore, it is critical in any process which uses and/or produces HCN that safety must be of highest priority. Thus, when increasing concentration of HCN of a process, extreme caution is needed to ensure safe operation of the process.

High concentrations of HCN in acrylonitrile systems are relatively unstable, and solid polymeric HCN can form in the heads column, reducing column pressure. The heads column is the distillation column in which HCN and ACRN are separated. The pressure drop raises the column temperature further favoring HCN polymerization. Solid polymerization products plug equipment, such as relief systems, valves, instruments, and piping, which in turn, increase risks associated with HCN.

Downtime associated with cleaning of the solids and other downstream process equipped is increased and results in substantial costs and loss production of ACRN and HCN. In U.S. Pat. Nos. 6,296,739 and 6,793,776, Godbole discloses methods to reduce the risk of HCN polymerization based on reducing the amount of aqueous layer in the heads column. Godbole's methods include increasing the reflux ratio of HCN to ACRN by adding recycled or pure HCN to the heads column to reduce the likelihood of polymer formation, among others. Common practice is to reduce column pressure thus lowering the column temperature.

There remains a need for co-production of acrylonitrile and HCN, wherein the weight ratio of ACRN and HCN is less than that provided in a conventional Sohio process. It is further desired to be able to vary this ratio. It is still further desired to avoid any negative effects on the acrylonitrile process, such as catalyst deactivation, and on downstream recovery and purification operations. It is further desired to have efficient conversion of methane to HCN, or at least avoid equipment and energy cost of producing methanol. It is further desired to maintain efficiency of oxygen consumption and to minimize formation of undesired by-products. It is still further desired to use existing acrylonitrile recovery and purification equipment. It is further critical that any increase in HCN concentration be performed in a manner that does not compromise safety. The present invention meets these needs.

SUMMARY OF THE INVENTION

The present invention is a process for co-manufacture of acrylonitrile and hydrogen cyanide comprising (a) combining a stream comprising hydrogen cyanide and an acrylonitrile reactor product stream, in an absorber column with water to produce a combined product stream, having a weight ratio of acrylonitrile to hydrogen cyanide of about 9 to 1 or less; and (b) treating the combined product stream sequentially in a recovery column, a decanter having an aqueous layer and an organic layer, and a heads column, wherein pH is controlled by addition of an acid at pH of 7.0 or less in the absorber column and the recovery column, and at pH less than 4.5 in the decanter and heads column. The weight ratio of acrylonitrile to hydrogen cyanide in the combined product stream is generally between 2 to 1 and 9 to 1, and may be between 2 to 1 and 5 to 1. The stream comprising hydrogen cyanide can be conveniently provided as a hydrogen cyanide product stream from a hydrogen cyanide synthesis reactor.

Thus, there is provided a process for hydrogen cyanide and acrylonitrile recovery and purification from which greater amounts of hydrogen cyanide are recovered relative to a conventional Sohio acrylonitrile process. The relative weight ratio of acrylonitrile to hydrogen cyanide can be controlled by controlling the feed rate of the stream comprising hydrogen cyanide in the process.

Essentially, according to the present invention, an acrylonitrile process and a hydrogen cyanide process can be operated in parallel and the product streams from the individual processes are combined in a single recovery/purification operation. Surprisingly, at relatively high concentrations of hydrogen cyanide in the process, HCN polymerization is substantially prevented and the process is operated in a safe manner. In addition, surprisingly the added HCN in the process can be simply combined with ACRN product stream for recovery and purification, without need for a separate purification system.

BRIEF DESCRIPTION OF THE DRAWINGS

FIG. 1 is a flow diagram of the process of this invention.

DETAILED DESCRIPTION OF THE INVENTION

Provided herein is a process for co-manufacture of hydrogen cyanide and acrylonitrile from separate reactor systems and combining in a single recovery/purification system. The process comprises combining a stream comprising hydrogen cyanide, such as a hydrogen cyanide reactor product stream, with an acrylonitrile reactor product stream, to produce a combined product stream, wherein the ratio of acrylonitrile and hydrogen cyanide in the combined product stream is 9 to 1 or less, preferably between 2 to 1 and 9 to 1, and introducing the combined product stream into a system for recovery and purification of acrylonitrile and hydrogen cyanide.

Acrylonitrile Reactor Product Stream

Acrylonitrile is produced in the present invention, for example, and preferably, by the Sohio process. In this process, propylene, propane or a combination thereof, reacts with ammonia and oxygen over a catalyst at elevated temperatures. Hydrogen cyanide and acetonitrile are produced as by-products. Any source of oxygen can be used. Typically, the oxygen source is air. Useful catalysts are known and are generally based on bismuth-molybdates.

The reaction is carried out a temperature of between about 260° C. and 600° C., preferably 310° C. to 510° C., more preferably 400° C. to 510° C. The pressure is typically 5 to 30 psig (34 to 207 kPa). The contact time is generally in the range of 0.1 to 50 seconds.

The acrylonitrile product stream (reactor effluent) is a gas stream comprising unreacted reactants, acrylonitrile, hydrogen cyanide, acetonitrile and water. The acrylonitrile product stream passes through a quencher into which water is fed to lower the temperature of this stream and to remove any unreacted ammonia. The unreacted ammonia can be recycled back into the process as a reactant. Alternatively, sulfuric acid may be added with the water to produce ammonium sulfate, which is removed as an aqueous stream.

It is understood that other ways of acrylonitrile manufacture are also possible, and the present invention is not limited to the Sohio process described above.

Stream Comprising Hydrogen Cyanide

The stream comprising hydrogen cyanide can be obtained from any source of hydrogen cyanide. Conveniently, hydrogen cyanide stream is provided as hydrogen cyanide product stream from a hydrogen cyanide synthesis reactor.

Hydrogen cyanide can be produced as a stand alone process, from the reaction of natural gas (methane), ammonia, and oxygen over platinum, platinum-rhodium, or a platinum-iridium alloy catalyst in gauze form at atmospheric pressures and at temperatures greater than 1000° C. in the Andrussow Process. Alternatively, hydrogen cyanide can be produced from methane and ammonia passed through porous ceramic tubes lined or coated with platinum, at about 1300° C. in the Degussa BMA Process. Detailed descriptions of these processes are provided, for example, in the Encyclopedia of Chemical Technology (Fourth Edition, Volume 7, pp 753 to 782) edited by Kirk-Othmer. It is understood that alternate methods of HCN production exist, and the present invention is not limited to those referred to hereinabove.

A hydrogen cyanide product stream comprises hydrogen cyanide and may also comprise unreacted reactants, such as but not limited to methane, oxygen, nitrogen, and additional impurities, such as but not limited to hydrogen.

Combined Product Stream

In the present invention, an acrylonitrile product stream and a stream comprising hydrogen cyanide are combined to create a combined product stream. The concentration of the each component in the combined product stream can be varied to produce a weight ratio of acrylonitrile to hydrogen cyanide ranging from 9 to 1, which is the typical weight ratio of acrylonitrile to hydrogen cyanide produced in a standard Sohio process, to 2 to 1 and may be between 2 to 1 and 5 to 1. Conveniently, this ratio can be adjusted by increasing or decreasing the rate of HCN being fed, such as increasing or decreasing rate of production from a HCN synthesis reactor. The combined product stream is introduced into a recovery and purification system.

The acrylonitrile product stream and the stream comprising hydrogen cyanide are combined in an absorber column of a recovery/purification operation. The streams are combined with water in the absorber column to provide an aqueous stream comprising hydrogen cyanide and acrylonitrile, having a weight ratio of acrylonitrile to hydrogen cyanide of about 9 to 1 or less;

A typical process of this invention can yield 360 to 400 million pounds (163,000 to 181,000 metric tons) of acrylonitrile and 40 to 150 million pounds (18,000 to 68,000 metric tons) of hydrogen cyanide per year. While additional hydrogen cyanide is produced, surprisingly there is no substantial loss in yield of acrylonitrile. That is, HCN and acrylonitrile can form adducts, which would decrease yield of acrylonitrile and it is surprising that given high concentration of HCN, no yield loss occurs. In addition, unlike methanol injection, there is no affect on capacity of the acrylonitrile reactor.

Recovery and Purification

The process of this invention comprises passing the combined product stream into an absorber column, recovery column, a decanter and a heads column. As is known to those skilled in the art, "column" herein refers to a distillation column. In the heads column, the crude HCN is separated from the crude ACRN, and sent to an HCN distillation column for further purification and then sent for additional reaction and/or to storage. The crude ACRN is sent from the heads column to a drying column then to a product column for further purification and storage. A detailed description of a typical recovery and purification process is known to those skilled in the art and is disclosed in U.S. Pat. No. 4,234,510 and Encyclopedia of Chemical Technology (Fourth Edition, Volume 7, pp 753 to 782) edited by Kirk-Othmer.

As will be appreciated by those skilled in the art, appropriate materials of construction should be used in the recovery and purification equipment, such as stainless steel rather than carbon steel, to protect equipment against higher concentrations of HCN relative to those of conventional Sohio acrylonitrile processes.

Flammable gases, such as methane and hydrogen, relative to a standard ACRN product stream are present in the absorber column as part of the combined product stream. Hydrogen, methane, and oxygen, as well as other non-absorbing gases, are separated from the combined product stream and removed as off-gas from the top of the absorber column for incineration, or further separation. As part of this invention it should be recognized by those skilled in the art, that the concentration of oxygen in the absorber column can become elevated and care should be taken to maintain an oxygen concentration below the explosion limit, for example, by adjusting the ratio of air to propylene being feed into the acrylonitrile reactor. Sensors and control systems are known and available commercially to make these adjustments.

In the present invention, the concentration of HCN present in the adsorber column is increased, for example up to about 3% by weight, relative to a typical Sohio process where the concentration of HCN is 1% by weight at the same location. Moreover, HCN concentration in the decanter can be as high as 20-30% by weight. Therefore, for safe operation, at the high HCN concentrations, conditions must be maintained to prevent HCN polymerization and/or decomposition.

In the process of this invention to accommodate the higher concentrations of HCN, there is provided a control system to monitor pH and temperature along the recovery/purification system. Specifically, through a combination of temperature control and pH control, conditions are maintained to prevent HCN polymerization from occurring. More specifically, in circulating aqueous streams, as are present in the absorber column, recovery column, and decanter, these streams are maintained at a pH of pH 7 or less. The aqueous feed to the absorber column generally has a pH of 5.5 to 7.0. The absorber column is preferably maintained at pH of 5.0 to 6.5, which is then fed to the recovery column. pH is monitored in the absorber column and acid is added if needed to lower pH, as described below.

Preferably the pH of the recovery column is near neutral pH, that is, pH of 6.8 to 7, for example, pH 6.8 to control acrolein in the system. If needed, a base, such as soda ash is added to the recovery column to raise pH.

Temperatures are also adjusted based on pH, as HCN polymerization is affect by a combination of pH and temperature.

Similarly, in organic streams, such as in the decanter, heads column and HCN column from which is recovered crude HCN, pH is controlled at pH less than 4.5, preferably at pH 3.8 to 4.2. Temperature is similarly controlled in combination with pH. For example, the decanter preferably has a temperature of less than about 50° C. and a pH of 3.8 to 4.2.

The control system can be any standard control system such as a distributed control system or other feedback control system. Devices are installed in the recovery/purification system, particularly on the decanter as part of the control system, to monitor and control the temperature and pH. The devices may include thermocouples, pH meters, feedback controllers, and control devices to adjust temperature, e.g., by increasing or decreasing coolant to a column and to adjust pH, e.g., by adding, increasing or decreasing flow of an acid to one or more of the absorber column, recovery column, decanter, heads column and HCN column. Under conventional operation, HCN concentrations are relatively low and acid addition was performed only in the heads column and in HCN distillation column.

The acid can be any acid capable of reducing the pH to below 4.5, preferably below 3.8. Preferably the acid is glycolic acid, acetic acid, phosphoric acid, succinic acid, lactic acid, formic acid, glyceric acid, citric acid, fumaric acid, citraconic acid, maleic acid, sulfamic acid, esters of these acids, and combinations of two or more thereof. More preferably, the acid is glycolic acid.

In addition to pH, temperature is controlled. The temperature of the decanter should be less than 50° C., preferably between 38° C. and 42° C. Process cooling is normally controlled by cooling water circulation including in the decanter. It is understood that others methods of cooling is acceptable provided it is compatible with the materials of construction and does not interfere with the recovery and purification.

The present invention has various advantages compared to currently practiced co-manufacture of acrylonitrile and hydrogen cyanide. The first advantage is the quantity of ACRN and HCN produced. ACRN reactor production is not decreased and the full potential of the plant is realized, while HCN production can be increased from 40 millions pounds (18,000 metric tons) of HCN in a typical non-methanol injection process, and from 50 million pounds (23,000 metric tons) per year in methanol injected process to ranges of 110 to 150 million pounds (50,000 to 68,000 metric tons) per year!

The quantity of HCN can also be selectively produced based on market need and can be reduced or increased without affecting the ACRN catalyst or process conditions.

An additional advantage is the elimination of the need to convert methane to methanol then to HCN improving the overall carbon balance of raw materials to final product. Another advantage of this invention is the ability to process large concentrations of HCN in the recovery and purification process while still preventing polymerization of HCN. Since risk of HCN polymerization increases with increasing HCN concentration it is surprising that the relatively high concentrations of HCN in the process of the present invention can be achieved with substantially no HCN polymerization, and maintaining safe operation.

Previous attempts to prevent polymerization added significant equipment and costs or reduced pressures which also can reduce total output. Using a process of this invention, downtime is reduced and plant output is consistent with a typical acrylonitrile process with minimal equipment costs.

DETAILED DESCRIPTION OF DRAWING

FIG. 1 is a general diagram of a hydrogen cyanide (HCN) and acrylonitrile (ACRN) process of this invention. An ACRN product stream 4 is obtained by the ammoxidation of propylene, ammonia, and air in ACRN reactor 2. A HCN product stream 3 is obtained by reaction of methane, ammonia, and air in a HCN reactor 1, such as an Andrussow reactor. The ACRN product stream 4 is transferred to a quench column 5 where the hot ACRN product stream is cooled with water spray containing sulfuric acid fed through line 6 to neutralize the unreacted ammonia in the ACRN product stream to produce ammonium sulfate which is removed from quench column 5 through line 8 to waste water column 9. Recovered HCN/ACRN is cycled back to quench column 5 through line 7. A waste water purge stream 10 is take from waste water column 9.

The cooled ACRN product stream 11 is then combined with the HCN product stream 3 in the absorber column 12, where the HCN and ACRN form a combined product stream as they are absorbed into an aqueous solution. Water is provided to the absorber column through line 13. Non-absorbed compounds are separated and removed as off-gas 15.

The aqueous solution containing the combined product stream 14 is then transferred to a recovery column 16 for product purification. The combined product stream 21 is fed to decanter 22. Water from stripper column 18 is fed through line 13 to absorber column.

A separate stream 17 is taken from the recovery column 16 and fed to stripper column 18 from which crude acetonitrile 19 is recovered and remaining aqueous stream 20 is fed back into recovery column 16. Crude acetonitrile 19 can be recovered or sent to incineration.

The product stream 21 from recovery column 16 is transferred to decanter 22 where the stream separates, forming an organic layer and an aqueous layer. The aqueous layer is separated and returned as reflux flow 29 to recovery column 16. The organic layer is transferred through line 28 to heads column 30 where it is separated into crude ACRN 31 and crude HCN 32.

The crude HCN 32 is sent to a HCN column 33, where the HCN is further purified and sent for storage (not shown) through line 40. Recovered ACRN 41 from HCN column 33 is returned to quench column 5 (line for return of recovered ACRN 41 from HCN column 33 to quench column 5 is not shown).

Crude ACRN 31 is sent to a drying column 34, from which water is removed through line 37. Dried ACRN 35 is transferred to ACRN product column 36 for further purification before being sent through line 39 to storage (not shown) from which waste material is removed from ACRN product column 36 through line 38.

Acetonitrile waste water stream 42 is combined with other waste water streams as combined waste water stream 43, which is collected and treated as needed.

Acid to control pH between pH 3.8 and 4.4 is added through any of lines 23, 25, 26, or 27 to absorber column 12, recovery column 16, decanter 22, heads column 28, and HCN column 33. An appropriate control system (not shown) is used to monitor pH and temperature at each location where HCN concentration is sufficiently high, that is, greater than 1% by weight, that there is increased risk of HCN polymerization.

EXAMPLES

The following Examples were performed in a flow system as illustrated in FIG. 1. For the Comparative Example, there was no HCN synthesis reactor and no HCN product stream present. The ACRN product stream (reactor effluent from acrylonitrile synthesis reactor) was treated in a quench column to reduce temperature to 46° C. and then fed to an absorber column. The HCN product stream (in Examples 1 and 2 only) was similarly quenched to a temperature of about 55° C. was combined with the ACRN product stream in the absorber column. The product stream (ACRN or combined stream) passed from the absorber column to a recovery column to a decanter, wherein an aqueous layer was separated from an organic layer, with the aqueous layer recycled to the recovery column and the organic layer fed to a heads column where crude HCN was separated from crude ACRN. Crude ACRN was removed from the bottom of the heads column and sent to a drying column and then further purification and packaging. Crude HCN was removed from the top of the heads column and sent to an HCN distillation column (HCN column) for further purification, reaction, if desired, and packaging.

COMPARATIVE EXAMPLE

For a nominal ACRN facility, capable of producing 180 million pounds (82 million kg) per year of acrylonitrile and 20 million pounds (9 million kg) of hydrogen cyanide, the facility produced about 50,000 pounds per hour, pph (23,000 kg per hour, kgph) of acrylonitrile and 6000 pph (3000 kgph) of HCN in a Sohio ammoxidation process. The effluent from the ACRN facility was an ACRN product stream having a temperature of about 450° C., which was fed to a quench column. After addition of sulfuric acid and water to remove unreacted ammonia, a stream at a temperature of 46° C. was fed to an absorber column, to a recovery column to a decanter, wherein an aqueous layer was separated from an organic layer, with the aqueous layer recycled to the recovery column and the organic layer fed to a heads column where crude HCN was separated from crude ACRN. Crude ACRN was removed from the bottom of the heads column and sent to a drying column and further purification and packaging. Crude HCN was removed from the top of the heads column and sent to an HCN distillation column for further purification, reaction, if desired, and packaging.

In this Comparative Example, the pH was monitored and controlled at the heads column, HCN column and drying column by adding glycolic acid to the column.

The product ratio of ACN to HCN after purification was 9 to 1.

Example 1

The process of the Comparative Example was repeated, with the following changes. A hydrogen cyanide reactor was operated producing an HCN product stream, which was combined with quenched stream from the ACRN process in the ACRN recovery/purification system used in the Comparative Example and as described above. ACRN was produced at the same rate as was produced in the Comparative Example. The amount of HCN produced from the ACRN reactor and hydrogen cyanide reactor was about 2.5 times the amount produced in Comparative Example.

High concentration of HCN in the streams, especially in the recovery column and decanter provide greatest concern for safety, where there are high concentrations of HCN in organic phases, susceptible to polymerization. In this Example 1, the pH was monitored and controlled at the absorber column, recovery column, decanter, heads column, and drying column by adding glycolic acid to the column or decanter, as needed to stabilize against polymerization.

Temperature was also monitored and controlled in each of these vessels by controlling flow of cooling water to the cooling system of each vessel.

After purification, the ratio of acrylonitrile to HCN was 3 to 1 with no substantially no polymerization of HCN.

Example 2

The process of Example 1 was repeated, but the amount of HCN produced was varied to provide ratios of ACRN to HCN of 2 to 1, 4 to 1 and 5 to 1 to show the ability to vary rate of co-manufacture of HCN and ACRN. In this Example, the pH was monitored and controlled at the absorber column, recovery column, decanter, heads column, and drying column by adding glycolic acid to the column or decanter, as needed to stabilize against polymerization. Thus, the process of this invention can provide varying amounts of HCN relative to ACRN with minimal need for added investment in recovery and purification operations. Polymerization of HCN was substantially prevented.

What is claimed is:

1. A process for co-manufacture of acrylonitrile and hydrogen cyanide comprising (a) operating an acrylonitrile process and a hydrogen cyanide process in parallel in separate reactor systems to produce an acrylonitrile reactor product stream and a stream comprising hydrogen cyanide, respectively, wherein the hydrogen cyanide is produced from reaction of natural gas (methane), ammonia, and oxygen or from methane and ammonia; (b) in a single recovery/purification system, combining the stream comprising hydrogen cyanide and the acrylonitrile reactor product stream in an absorber column with water, to produce a combined product stream, having a ratio of acrylonitrile to hydrogen cyanide of about 9 to 1 or less; and (b) treating the combined product stream sequentially in a recovery column, a decanter having an aqueous layer and an organic layer, and a heads column, wherein pH is controlled by addition of an acid at pH of 7.0 or less in the absorber column and the recovery column, and at pH less than 4.5 in the decanter and heads column.

2. A process according to claim 1 wherein the weight ratio of acrylonitrile to hydrogen cyanide in the combined product stream is between 2 to 1 and 9 to 1.

3. A process according to claim 1 wherein the weight ratio of acrylonitrile to hydrogen cyanide in the combined product stream is between 2 to 1 and 5 to 1.

4. A process according to claim 1 wherein the pH in the decanter was controlled at pH of 4.2 or less.

5. A process according to claim 1 wherein step (b) further comprises separating a crude HCN stream from a crude acrylonitrile stream in the heads column, treating the crude HCN stream in a HCN distillation column, and treating the crude acrylonitrile stream in a drying column, wherein pH is controlled in the HCN distillation column at pH less than 4.5.

6. A process according to claim 1 wherein step (b) further comprises separating a crude HCN stream from a crude acrylonitrile stream in the heads column, treating the crude HCN stream in a HCN distillation column, and treating the crude acrylonitrile stream in a drying column, wherein pH is controlled in the HCN distillation column at pH less than 4.5.

7. A process according to claim 5 wherein pH is controlled in the absorber column at pH 5.5 to 7.0, pH is controlled in the recovery column at pH 6.8 to 7.0; and pH is controlled in the decanter at pH 3.8 to 4.2.

8. A process according to claim 6 wherein pH is controlled in the absorber column at pH 5.5 to 7.0, pH is controlled in the recovery column at pH 6.8 to 7.0; and pH is controlled in the decanter at pH 3.8 to 4.2.

9. A process according to claim 7 wherein pH is controlled in the absorber column at pH 5.5 to 7.0, pH is controlled in the recovery column at pH 6.8 to 7.0; and pH is controlled in the decanter at pH 3.8 to 4.2.

10. A process according to claim 4 wherein pH is controlled in the absorber column at pH 5.5 to 7.0, pH is controlled in the recovery column at pH 6.8 to 7.0; and pH is controlled in the decanter at pH 3.8 to 4.2.

11. A process according to claim 9 wherein the temperature in the decanter is less than 50° C.

12. A process according to claim 10 wherein the temperature in the decanter is less than 50° C.

13. A process according to claim 2, wherein the concentration of hydrogen cyanide in the absorber column is between 1 and 3% by weight.

14. A process according to claim 2, wherein the concentration of hydrogen cyanide in the decanter is between 20 and 30% by weight.

15. A process according to claim 1 wherein the acid is glycolic acid, acetic acid, phosphoric acid, succinic acid, lactic acid, formic acid, glyceric acid, citric acid, fumaric acid, citraconic acid, maleic acid, sulfamic acid, esters of these acids, or a combination of two or more thereof.

16. A process according to claim 1 wherein the acid is glycolic acid, acetic acid, phosphoric acid, succinic acid, lactic acid, formic acid, glyceric acid, citric acid, fumaric acid, citraconic acid, maleic acid, sulfamic acid, esters of these acids, or a combination of two or more thereof.

17. A process according to claim 16 wherein the acid is glycolic acid.

18. A process according to claim 17 wherein the acid is glycolic acid.

* * * * *